United States Patent [19]

Mazzocco et al.

[11] Patent Number: 4,715,373
[45] Date of Patent: Dec. 29, 1987

[54] DEVICES FOR IMPLANTATION OF DEFORMABLE INTRAOCULAR LENS STRUCTURES

[76] Inventors: Thomas R. Mazzocco, 16534 Buchet Dr., Granada Hills, Calif. 91344; Mary T. Frenchik, 22240 Schoenborn St., Canoga Park, Calif. 91304

[21] Appl. No.: 781,399

[22] Filed: Sep. 27, 1985

[51] Int. Cl.$^4$ .............................................. A61B 17/36
[52] U.S. Cl. .................. 128/303 R; 128/321; 623/6
[58] Field of Search .............. 128/321, 303 R; 623/6; 604/14, 104, 107, 322-324, 343, 354

[56] References Cited

U.S. PATENT DOCUMENTS

| 4,393,872 | 7/1983 | Reznik et al. | 128/321 |
| 4,573,998 | 3/1986 | Mazzocco | 128/321 |
| 4,592,347 | 6/1986 | Mahruki | 128/321 |
| 4,600,003 | 7/1986 | Lopez | 128/303 R |
| 4,600,004 | 7/1986 | Lopez et al. | 128/303 R |

FOREIGN PATENT DOCUMENTS 2114315  8/1983  United Kingdom ................... 623/6

*Primary Examiner*—Stephen C. Pellegrino
*Assistant Examiner*—John D. Ferros
*Attorney, Agent, or Firm*—Frank Frisenda, Jr.

[57] ABSTRACT

The invention provides unique devices for implantation of deformable intraocular lens structures for surgical placement in the eye. In one embodied form, the inventive device comprises a generally cylindrical disarticulating lens holding member at a distal end of the device for receiving an intraocular lens having a deformable optical zone portion therein; a concentrically aligned sleeve for exerting a prescribed compressive force upon the intraocular lens once contained within the lens holding member; and a collar element disposed at a proximate end of the surgical device for facilitating placement of the lens and for effecting release of the compressed lens through a relatively small incision made in the ocular tissue. Accordingly, by use of the unique implantation tool, an ophthalmic surgeon may inspect the intraocular lens held within the device for appropriate optical characteristics prior to manipulation within the eye, and ensure compression of the deformable lens to a prescribed cross-section for insertion through the small incision made in the ocular tissue and ensure convenient release and placement of the deformed lens, but without widening the ocular wound.

13 Claims, 19 Drawing Figures

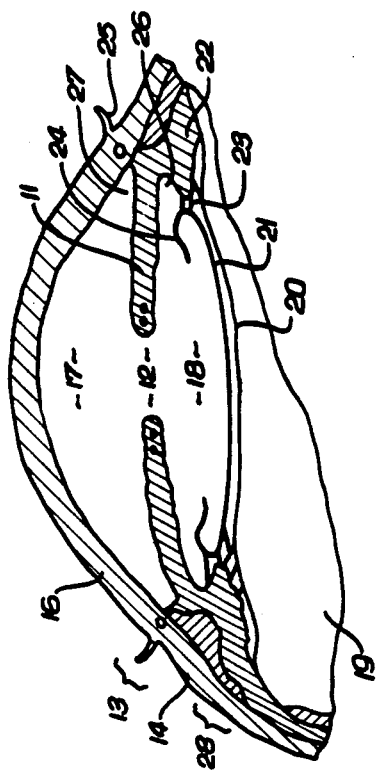
Fig. 2.
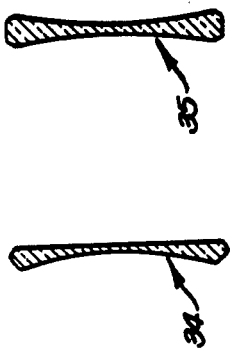
Fig. 4.
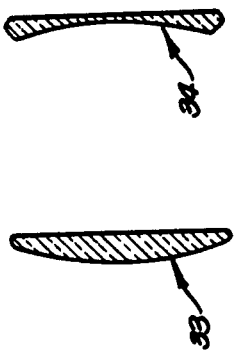
Fig. 5.
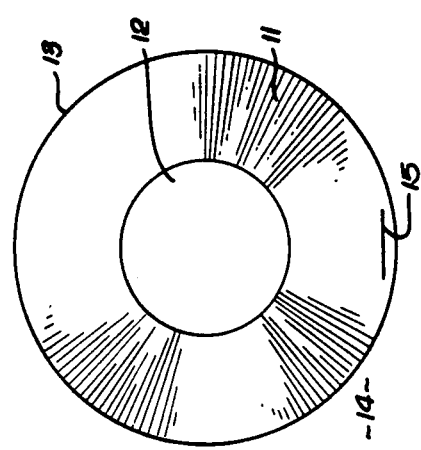
Fig. 1.
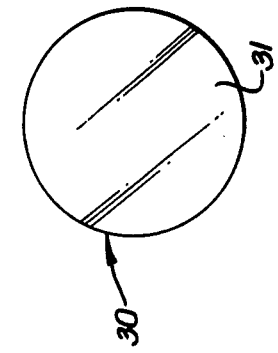
Fig. 3.

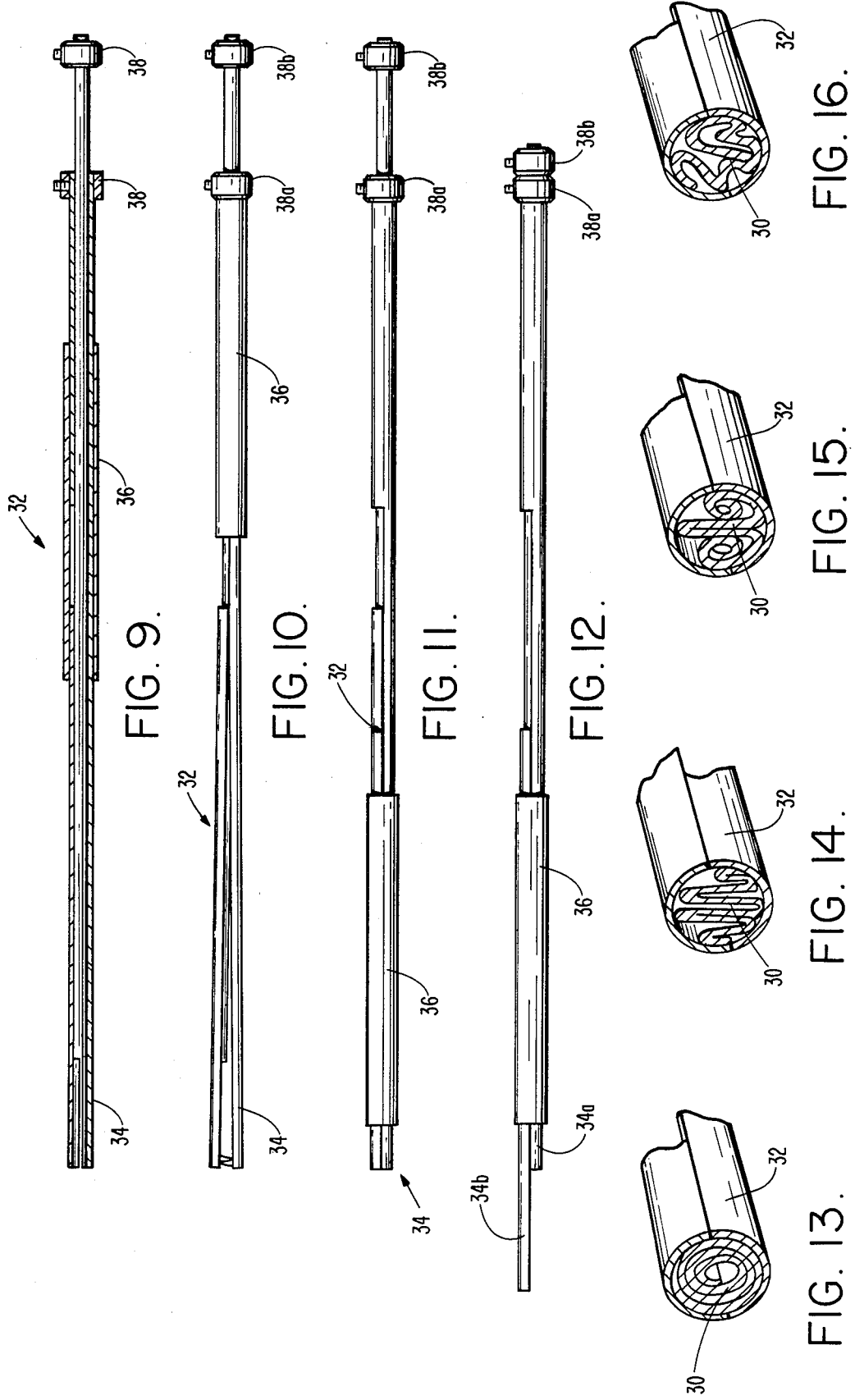

DEVICES FOR IMPLANTATION OF DEFORMABLE INTRAOCULAR LENS STRUCTURES

BACKGROUND OF THE INVENTION

Intraocular lenses have gained wide acceptance in replacement of human crystalline lens after a variety of cataract removal procedures. The human crystalline lens is generally recognized to be a transparent structure having a thickness of about 5 millimeters and a diameter of about 9 millimeters. The lens is suspended behind the iris by zonula fibers which connect the lens to the ciliary body. A lens capsule surrounds the lens, the front portion of the capsule being commonly known as the anterior capsule and the back portion commonly known as the posterior capsule.

Numerous procedures for the removal of cataracts have been developed in which the lens is removed from the eye and replaced by an artificial lens implant. The extraction procedure may generally be categorized as intracapsular (in which the lens is removed together with the lens capsule) and extracapsular (in which the anterior capsule is removed with the lens, and the posterior capsule is left intact).

Since Ridley implanted the first artificial lens in about 1949, the problems associated with cataract extraction and lens implantation have received a great deal of attention from ophthalmic surgeons. Various types of artificial lenses have been proposed, and appropriate surgical procedures have been developed which strive to reduce patient discomfort and to reduce postoperative complications. Reference is made in this connection to *Pseudophakos* by N. Jaffe, et al.; "History of Intraocular Impants" by D. P. Choyce (Annals of Ophthalomology, October 1973); U.S. Pat. No. 4,251,887 issued to Anis on Feb. 24, 1981; U.S. Pat. No. 4,092,743 issued to Kelman on Nov. 8, 1977; "Comparison of Flexible Posterior Chamber Implants", presented at the American Intraocular Implant Society Symposium Apr. 23, 1982, by Charles Berkert, M.D.; and "the Simcoe Posterior Lens' (Cilco, Inc. 1980); pending U.S. patent application Ser. No. 346,105 for "Deformable Intraocular Lens Structures and Methods and Devices for Implantation" filed Feb. 15, 1982 by the inventor Thomas R. Mazzocco, and pending U.S. patent application Ser. No. 400,665 for "Improved Fixation System for Intraocular Lens Structures", filed July 22, 1982, the latter applications being commonly assigned to the instant Assignee; which disclosures are hereby incorporated by this reference.

Of particular interest in the context of the present invention is the development of surgical techniques requiring relatively small incisions in the ocular tissue for the removal of cataracts as disclosed in U.S. Pat. No. 4,002,169 and U.S. Pat. No. 3,996,935. A number of skilled artisans have disclosed intraocular lens structures comprising an optical zone portion generally made of rigid materials such as glass or plastics suitable for optical use.

However, one of the principal disadvantages of the conventional rigid intraocular lens is that implantation of the lens requires a relatively large incision in the ocular tissue. This type of surgical procedure leads to a relatively high complication rate, among other disadvantages. For instance, the serious dangers associated with implantation of a rigid lens structure include increased risks of infection, retinal detachment, and laceration of the ocular tissues, particularly with respect to the pupil.

Accordingly, those skilled in the art have recognized a significant need for surgical tools for implantation of deformable intraocular lens structures which afford the clinical advantages of using relatively small incision techniques, which provides a safer and more convenient surgical procedure. In particular, those skilled in the art of deformable intraocular lenses and methods and devices for implantation, have also recognized a significant need for surgical tools which do not require widening of the wound made in the ocular tissue during or after implantation, but will deform the intraocular lens to a predetermined cross section in a stressed state and which will allow the ophthalmic surgeon to inspect the lens prior to implantation without manipulation in the eye. The present invention fulfills these needs.

SUMMARY OF THE INVENTION

This invention relates to unique devices for implantation of deformable intraocular lens structures and for surgical placement in the eye. In more detail, and in one embodied form of the invention, the surgical device comprises a generally cylindrical disarticulating lens holding means at a distal end of the device for receiving an intraocular lens having a deformable optical zone portion therein; a concentrically aligned sleeve for exerting a prescribed compressive force upon the intraocular lens once contained within the lens holding means; and tab means disposed at a proximate end of the surgical device for facilitating placement of the lens and for conveniently effecting release of a deformed lens 30 through a relatively small incision made in the ocular tissue.

The unique devices for implantation are preferably fabricated from autoclavible materials such as stainless steel or from a disposable rigid plastics such as medical grade ABS or the like.

The lens holding means is adapted to receive at least a portion of a deformable optical zone portion of the lens having prescribed memory characteristics, and exerts a deforming force on the optical zone by compressing, rolling, folding or by a combination thereof, the optical zone to a diameter of about 80% or less of the cross-sectional diameter of the optic in an unstressed state. Additionally, the lens holding means allows the deformed lens to return to its original configuration, full size and fixed focal length after insertion in the eye but without requiring a widening of the optical wound. The lens holding means can be fabricated to partially or fully encase and deform the intraocular lens to permit placement of the lens within the eye.

Thus, the present invention offers a unique implantation system and surgical tools for correction of or replacement of a human crystalline lens, for instance, after cataract removal by way of small incision technique. By use of the unique implantation tools, an ophthalmic surgeon may inspect the intraocular lens for appropriate optical characteristics custom fitted to a patient's individual requirements prior to manipulation within the eye. The tools further insure compression of the deformable lens to a prescribed cross-section in a stressed state for insertion through the small incision made in the ocular tissue and ensure convenient release and placement of the deformed lens, but without widening the ocular wound made for insertion.

The above and other objects and advantages will become apparent from the following more detailed description of the invention taken in conjunction with the drawings.

BRIEF DESCRIPTION OF THE DRAWINGS

FIG. 1 is stylized frontal view of the human eye illustrating a relatively small surgical incision made in the ocular tissue relative to major eye components for purposes of referencing the description of devices for implantation of deformable intraocular lens structures in accordance with the present invention;

FIG. 2 is partially side sectional view of the human eye shown in FIG. 1 illustrating the internal condition of the ocular area after extra capsular cataract extraction in accordance with conventional procedure;

FIG. 3 is a frontal elevational view of one embodied form of a deformable intraocular lens structures to be inserted in the eye in accordance with the present invention;

FIG. 4 is a side sectional view of the intraocular lens shown in FIG. 3 of the biconvex lens specie;

FIG. 5 is side sectional view of the intraocular lens shown in FIG. 3 of the plano convex lens specie;

FIG. 6 is side sectional view of the intraocular lens specie shown in FIG. 3 of the plano concave lens specie;

FIG. 7 is a side sectional view of the intraocular lens shown in FIG. 3 of the bioconcave lens specie;

FIG. 8 is a side sectional view of the intraocular lens shown in FIG. 3 of the concave-convex lens specie;

FIG. 9 is side sectional view of one embodied form of the unique device for implantation of deformable lens structures for surgical placement in the eye;

FIG. 10 is a side view of the surgical device depicted in FIG. 9 illustrating a generally cylindrical disarticulating lens holding member at a distal end of the device; a concentrically aligned sleeve in a retracted position for exerting a prescribed compressive force upon the intraocular lens once contained within the lens holding member;

FIG. 11 is a side view of the unique device for implantation depicted in FIG. 10 and showing the aligned sleeve in a forward position on the lens holding member thus exerting a prescribed compressive force upon the intraocular lens once contained within the lens holding member;

FIG. 12 is the inventive device for implantation depicted in FIG. 11 and illustrating the lens holding member in a disarticulated position for effecting release of the compressed lens through a relatively small incision made in the ocular tissue;

FIG. 13 is an enlarged fragmentary view of the distal end of the device depicted in FIG. 9 illustrating the lens in a rolled condition after undergoing deformation during the implant procedure;

FIG. 14 is an enlarged fragmentary view of the distal end of the device depicted in FIG. 9 illustrating the lens in a folded condition after undergoing deformation during the implant procedure;

FIG. 15 is an enlarged fragmentary view of the distal end of the device depicted in FIG. 9 illustrating the lens in a partly rolled and partly folded condition;

FIG. 16 is an enlarged fragmentary view of the distal end of the device depicted in FIG. 9 illustrating the lens in a random "crumple" fold condition.

DESCRIPTION OF THE PREFERRED EMBODIMENTS

Figure 17:
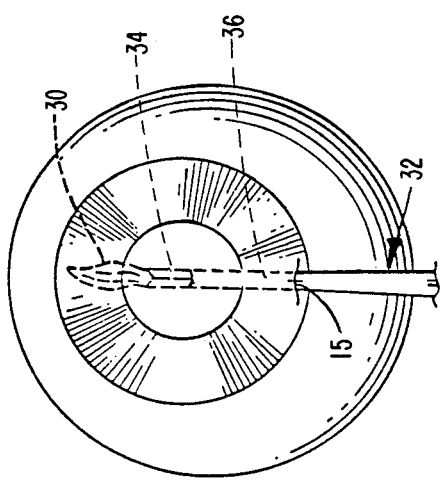
FIG. 17 is a frontal sectional view of an implant procedure utilizing a surgical tool in one embodied form to place the intraocular lens in a posterior chamber through the pupil.

The present invention provides unique devices for implantation of deformable intraocular lens structures for surgical placement in the eye. The surgical tools in accordance with the present invention, may be utilized in a wide variety of procedures for correction of or replacement of a human crystalline lens. Ihe inventive devices comprise means for deforming the optical zone portion of the intraocular lens structure by compressing, rolling, folding, or by a combination of these techniques to deform the optical zone portion to a diameter of 80% or less than the cross-sectional diameter of the optic during insertion into the eye yet permit the deformed lens to return to its original configuration, size and fixed focal length once implanted in the eye, thereby providing a safer, more convenient, and more comfortable surgical procedure.

In one embodied form, the inventive device comprises a generally cylindrical disarticulating lens holding member at a distal end of the device for receiving the intraocular lens therein; a concentrically aligned sleeve for exerting a prescribed compressive force on at least a portion of the intraocular lens once held by the lens holding member; and tab means disposed at a proximate end of the surgical device and for effecting release and placement of the deformed lens through a relatively small incision made in the ocular tissue.

Referring now to the drawing, denoted FIG. 1, there is shown a stylized frontal view of an eye illustrating the major ocular components; iris 11, pupil 12, limbus 13, sclera 14 relative to small incision 15 made in the ocular tissue, for instance, for implantation of an intraocular lens in accordance with the present invention.

FIG. 2 represents a side cross-sectional view of the eye shown in FIG. 1 and illustrates the major ocular components in more detail. The cornea 16 is composed of clear tissue which connects to the sclera 14 at the limbus 13. The anterior segment of the eye is divided into two principal chambers by the iris 11 and pupil 12. The anterior chamber 17 is defined by the space between the cornea 16 and the iris 11. A posterior chamber 18 is defined by the space between the iris 11 and the vitreous 19.

In surgical procedures commonly known as intracapsular cataract extraction, the posterior chamber 18 is bounded by the hyloid membrane 20. In surgical procedures commonly known as extracapsular cataract extraction, the posterior chamber 18 is bounded by the posterior capsule 21 attached to the ciliary body 22 by means of zonular fibers 23. Portions of the anterior capsule may remain as flaps 24, creating, with the posterior capsule, 21 the ocular portion commonly known as the "capsular bag". The posterior chamber 18 peripheral area between the iris 11 and the extension of the ciliary body 22 is referred to as the ciliary sulcus 26. The anterior chamber peripheral area between the cornea 16 and iris 11 is referred to as the angle 27 of the eye. The area of the sclera posterior to the plane of the iris and anterior to the vitreous 19 is known as pars plana 28.

With the foregoing reference ocular components in mind, it is a principle feature of the class of intraocular lens structures having a deformable optical zone portion such that the lens with optional fixation appendages can be deformed by compressing, rolling, folding or stretching to a diameter of 80% or less of the cross-sectional diameter of the optic during insertion into the eye, yet return to its original full size and fixed focal length once implanted in the eye. Accordingly, the deformable intraocular lens structures can be implanted through smaller incisions made in the ocular tissue than would be possible with any rigid intraocular lens of comparable size.

FIG. 3 depicts an intraocular lens 30 of the deformable class of intraocular lens structures which is suitable for use an artificial lens implant. In the embodied form shown, there are no fixation appendages and the lens comprises a deformable optical zone portion 31 imparted with desirable memory characteristics, appropriate structural dimensions, and composed of a deformable material such that the lens can be deformed to an appropriate size for insertion into the eye.

Typically, the optical zone portion 31 of the lens 30 is composed of one or more suitable materials such as a polyurethane elastomer, silicone elastomer, hydrogel polymer collagen compounds, organize or synthetic gel compounds and combinations thereof. The optical zone portion 31 of the lens can be fabricated having a base member composed of any of the foregoing materials, and further comprise a surface layer or layers of a second or third material. Moreover, the lens may be tinted, colored or fabricated with occluded portions to yield desire transmission effects.

As shown in FIGS. 4, 5, 6, 7, and 8, the deformable lens can be fabricated having a wide variety of cross-sections designed for replacement of the surgically removed human crystalline lens for for refractive correction without removal of the human crystalline lens. In this respect, the FIGS. 4 through 8 illustrate respectively a convex lens, a plano convex lens, a plano concave lens, a biconcave and a concave-convex lens.

Additionally, the intraocular lens structure may be provided with means for assisting, suturing, manipulation, or fluid flow through the lens. In this respect, the lens may be provided with one or more holes suitable located which may extend entirely through the cross-section of the lens or partially through the cross-section of the lens as an indentation for facilitating maneuvering of the lens during surgical procedure.

Further, the intraocular lens structures may comprise integral or nonintegral appendages to facilitate positioning of the lens within the eye. Optionally, the lens may be provided with appendages of the compressible-integral support element type or appendage of the uniplanar type with the optical zone portion of the lens.

The lens may also be provided with a plurality of holes therethrough and angulated support appendages with respect to the plane of the optic. Such appendages may be composed of any suitable material and may be selected from a material different from that of the optical zone portion of the lens.

As will readily be appreciated by those skills in the art, the foregoing specific embodiments of the deformable intraocular lens structures are merely illustrative of a wide variety of intraocular lens structures included in the spirit and scope of this invention. In this respect, it should be understood that the provision of appendages and means for facilitating manipulating, fixation, or fluid flow through the lens are optional. The latter means includes holes, openings, depressions and/or passage ways to aid the surgical procedure.

Those skilled in the art will further appreciate that the intraocular lens implant can be fixated in the eye in a wide variety of locations and that a wide variety of supporting appendages may optionally be included with the deformable optical zone portion of the lens to fixate the lens in the desired position.

Referring now to FIG. 9, there is depicted one embodied form of a unique device for implantation of deformable lens structures and for surgical placement in the eye. In more details, the surgical device 32 comprises a generally cylindrical disarticulating lens holding means 34 at a distal end of the device for receiving an intraocular lens 30 having a deformable optical zone portion therein; a concentrically aligned sleeve 36 for exerting a prescribed compressive force upon the intraocular lens 30 once contained within the lens holding means 34; and tab means 38 disposed at a proximate end of the surgical device 32 for facilitating placement of the lens 30 and for conveniently effecting release of the deformed lens 30 through a relatively small incision made in the ocular tissue (not shown).

The unique device 32 for implantation is preferably fabricated from autoclavible material such as stainless steel or from a disposable rigid plastic such as medical grade ABS or the like.

The lens holding means 34 is adapted to receive at least a portion of a deformable optical zone portion 30 of the lens having prescribed memory characteristics, and exerts a deforming force on the optical zone 30 by compressing, rolling, folding or by a combination thereof, the optical zone portion to a diameter of about 80% or less of the cross-sectional diameter of the optic in an unstressed state. Additionally, the lens holding means 34 allows the deformed lens to return to its original configuration (FIG. 3), full size and fixed focal length after insertion in the eye but without requiring a widening of the optical wound. The lens holding means may generally be described as a rigid hollow container, preferably cylindrical, to partially or fully encase and deform the intraocular lens to permit placement of the lens within the eye.

As shown in FIG. 10, the embodied surgical device depicted in FIG. 9 includes a generally cylindrical disarticulating lens holding member 34 at a distal end of the device 32. The concentrically aligned sleeve 36 is slideable between retracted positions in which no or little compressive force is exerted on the lens, or may be slid forward as depicted in FIG. 11, thus exerting a prescribed compressive force upon the intraocular lens 30 once contained within the lens holding member 34.

FIG. 12 illustrates the lens holding member 34 in a disarticulated position for effecting release of the compressed lens 30 through a relatively small incision made in the ocular tissue.

FIG. 23 is an enlarged fragmentary view of the distal end of the device 32 illustrating the lens 30 in a folded condition after undergoing deformation during the implant procedure.

FIG. 14 is another enlarged fragmentary view of the distal end of the device 32 illustrating the lens 30 in a folded condition after undergoing deformation during the implant procedure.

FIG. 15 in another enlarged fragmentary view of the distal end of the device 32 illustrating the lens 30 in a partly rolled and partly folded condition after undergoing deformation during the implant procedure.

FIG. 16 depicts yet another enlarged fragmentary view of the distal end of the device 32 illustrating the lens 30 in a random "crumple" folded condition after undergoing deformation during the implant procedure.

As shown in FIG. 17, the inventive device 32 may be constructed to only partially hold and encase the lens 30 to assist placement of the lens in the posterior chamber through the pupil. It should be understood however, that these devices 32 can readily position the lens 30 in the anterior chamber of the eye as well.

As previously mentioned, the present invention is readily adapted to implant lens for refractive correction of the human crystalline lens without the removal thereof. As shown in FIG. 16, the intraocular lens 30 is placed in the posterior chamber between the iris and human crystalline lens as shown.

Figure 19:
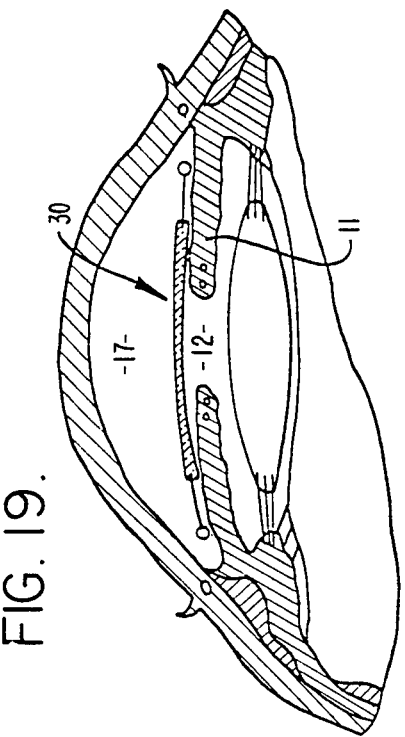
FIG. 19 is a cross-sectional view of a eye with human crystalline lens intact and an intraocular lens in position in the anterior chamber of the eye for corrective purposes.
Figure 18:
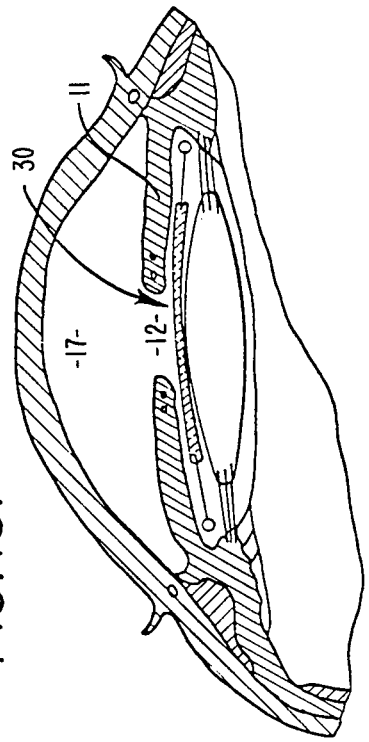
FIG. 18 is a side sectional view of an eye with natural crystalline lens intact and an intraocular lens of the corrective type in position in the posterior chamber between the iris and the human crystalline lens.

FIG. 19 depicts an alternate positioning of lens 30 where placement of the lens in the anterior chamber of the eye is effected with the natural crystalline lens still intact and in place.

As further seen in FIG. 9 and FIG. 10, the generally cylindrical disarticulating holding member 34 comprises two concentrically aligned cylindrical sections 34A and 34B, each provided with tab means 38A and 38B. Preferably, the tab means 38 is in the form of a collar element disposed at a proximate end of the surgical device. One of the cylindrical sections 34A of the holding member 34 is hemicylindrical.

As seen in FIG. 10, when the cylindrical section 34A is aligned with the cylindrical section 34B such that the distal ends of the device 32 are commensurate in length with each other, the distal end of the cylindrical device 32 provides a split rod section for receiving the deformable lens therein.

Upon receiving the intraocular lens in the cylindrical sections 34A and 34B, the sleeve is manually pushed forward to exert a prescribed compressive force upon the intraocular lens once contained within the lens holding member 34 as shown in FIG. 11.

After containment in the device 32, the deformed lens contained within the disarticulating holding member 34 may be conveniently released by an ophthalmic surgeon by utilizing tab means 38. As such shown in FIG. 12, the tab means 38, in this instance a collar element 38B is pushed forward by the surgeon to be contiguous with the collar member 38B thereby forcing the deformed lens 30 from the holding member 34.

Accordingly, the present invention offers a unique implantation tool for correct of or replacement of human crystalline lens after, for instance, cataract removal by way of small incision technique. The inventive tools therefore provide an implantation system with attendant surgical safety, convenience and comfortable manipulation in the eye.

The described lens implantation devices, thus minimize the principal disadvantages attendent with conventional rigid intraocular lens implantation systems which require a relatively large incision in the ocular tissue which, among other disadvantages, leads to a relatively high complication rate and longer patient recovery time.

It will be apparent from the foregoing that while particular forms of the invention have been illustrated and described, various modifications can be made without departing from the spirit and the scope cf the invention. Accordingly, it is not intended that the invention be limited, except as by the appended section.

We claim:

1. A surgical device for implantation of deformable intraocular lens in the eye through a relatively small incision made in the ocular tissue, said device comprising:
   (a) A generally cylindrical disarticulating holding means at the distal end of the device for receiving an intraocular lens having a deformable optical zone portion therein; said holding means comprising two concentrically aligned cylindrical half sections;
   (b) A concentrically aligned sleeve for exerting a prescribed compressive force upon the intraocular lens once contained within the lens holding means, said concentrically aligned sleeve being slidable between retracted positions in which no or little compressive force is exerted on said lens, and a forward position in which a prescribed compressive force is exerted upon at least a portion of said intraocular lens once contained within said lens holding means; and
   (c) Tab means disposed at a proximate end of the surgical device for facilitating placement of the lens and for convenient effecting release of the deformed lens through a relatively small incision made in the ocular tissue.

2. The surgical device as defined in claim 1 wherein said surgical device is fabricated from autoclavable material.

3. The surgical device as defined in claim 1 wherein said device is fabricated from stainless steel.

4. The surgical device as defined in claim 1 wherein said device is fabricated from medical grade plastic material.

5. The surgical device as defined in claim 1 wherein said device is fabricated from medical grade ABS plastic.

6. The surgical device as defined in claim 1 wherein said lens holding means is adapted to received at least a portion of said deformable optical zone portion of said lens.

7. The surgical device as defined in claim 1 wherein said lens holding means exerts a deforming force on the optical zone portion of said lens by compressing said optical zone to a diameter of about 80% of less of the cross-sectional diameter of the optic in an unstressed state.

8. The surgical device as defined in claim 1 wherein said lens holding means exerts a deforming force on the optical zone portion of said lens by rolling said optical zone to a diameter of about 80% of less of the cross-sectional diameter of the optic in an unstressed state.

9. The surgical device as defined in claim 1 wherein said lens holding means exerts a deforming force on the optical zone portion of said lens by folding said optical zone to a diameter of about 80% of less of the cross-sectional diameter of the optic in an unstressed state.

10. The surgical device as defined in claim 1 wherein said tab means disposed at a proximate end of said surgical device is a collar member.

11. The surgical device as defined in claim 1 wherein said lens holding means allowed the deformed intraocular lens to return to its original configuration, full size and fixed focal length after insertion in the eye but without requiring a widening of the optical wound.

12. The surgical device as defined in claim 1 wherein said lens holding means comprises a rigid hollow container to partially or fully encase and deform said intraocular lens to permit placement of said lens within the eye.

13. The surgical device as defined in claim 12 wherein said rigid hollow container is of a cylindrical cross-section.

* * * * *